(12) United States Patent
Palmer et al.

(10) Patent No.: US 7,655,050 B2
(45) Date of Patent: Feb. 2, 2010

(54) COMPUTER CONTROLLED PROSTHETIC KNEE DEVICE

(75) Inventors: Michael L. Palmer, Ladera Ranch, CA (US); Charles R. Bisbee, III, Mission Viejo, CA (US)

(73) Assignee: Freedom Innovations, LLC, Irvine, CA (US)

( * ) Notice: Subject to any disclaimer, the term of this patent is extended or adjusted under 35 U.S.C. 154(b) by 717 days.

(21) Appl. No.: 11/460,956

(22) Filed: Jul. 28, 2006

(65) Prior Publication Data

US 2007/0027555 A1 Feb. 1, 2007

Related U.S. Application Data

(60) Provisional application No. 60/703,588, filed on Jul. 29, 2005.

(51) Int. Cl.
   A61F 2/64 (2006.01)
   A61F 2/68 (2006.01)
(52) U.S. Cl. .................................................. 623/45
(58) Field of Classification Search .............. 623/39–46
   See application file for complete search history.

(56) References Cited

U.S. PATENT DOCUMENTS

| | | | |
|---|---|---|---|
| 5,062,857 A * | 11/1991 | Berringer et al. ............... | 623/25 |
| 5,190,126 A | 3/1993 | Curnutt | |
| 5,383,939 A | 1/1995 | James | |
| 5,571,205 A | 11/1996 | James | |
| 5,888,212 A | 3/1999 | Petrofsky et al. | |
| 6,113,642 A | 9/2000 | Petrofsky et al. | |
| 6,423,098 B1 | 7/2002 | Biedermann | |
| 6,443,993 B1 | 9/2002 | Koniuk | |
| 6,517,585 B1 | 2/2003 | Zahedi et al. | |
| 6,610,101 B2 | 8/2003 | Herr et al. | |
| 6,673,117 B1 | 1/2004 | Soss et al. | |
| 6,719,806 B1 | 4/2004 | Zahedi et al. | |
| 6,740,125 B2 * | 5/2004 | Mosler .......................... | 623/45 |
| 6,755,870 B1 | 6/2004 | Biedermann et al. | |
| 6,764,520 B2 | 7/2004 | Deffenbaugh et al. | |
| 6,978,872 B2 | 12/2005 | Turner | |

* cited by examiner

*Primary Examiner*—Bruce E Snow
(74) *Attorney, Agent, or Firm*—Luce Forward Hamilton and Scripps; Marlan Walker; Peter Gluck

(57) ABSTRACT

A prosthetic knee provides a single axis of rotation and includes a hydraulic damping cylinder, a microprocessor, and sensors. Based on input from the sensors, the microprocessor selects a flow path within the hydraulic cylinder in order to provide the proper amount of knee resistance to bending for a given situation. The resistance of each flow path within the hydraulic cylinder is manually preset. Changes in gait speed are accommodated by employing a hydraulic damper with intelligently designed position sensitive damping. Moreover, the knee need not be un-weighted to transition from the stance phase to the swing phase of gait. As a result, the knee safely provides a natural, energy efficient gait over a range of terrains and gait speeds and is simpler, less costly, and lighter weight than the prior art.

14 Claims, 6 Drawing Sheets

$R_E$ = EXTENSION RESISTANCE = f(PISTON VELOCITY, PISTON POSITION,
(NEEDLE VALVE WITH   VALVE POSITION)
SHIM STACK)

$R_{LC}$ = LOW FORCE COMPRESSION = f(PISTON VELOCITY, PISTON POSITION,
RESISTANCE   AIR PRESSURE)
(PRESSEURE SENSITIVE
CONTROL VALVE)

$R_{HC}$ = HIGH FORCE COMPRESSION = f(PISTON VELOCITY, VALVE POSITION)
RESISTANCE
(NEEDLE VALVE)

US 7,655,050 B2

COMPUTER CONTROLLED PROSTHETIC KNEE DEVICE

RELATED APPLICATION

This application claims the benefit of and Paris Convention priority of U.S. Provisional Application Ser. No. 60/703,588 filed on Jul. 29, 2005, the contents of which are hereby incorporated by reference as if fully disclosed herein.

BACKGROUND OF THE DISCLOSURE

The present disclosure relates generally to prosthetic devices and, more particularly, to prosthetic knees imparted with electronically improved motility and safety.

Attempts have been made to overcome the drawbacks associated with the function of prosthetic knees by incorporating actuators that are actively, or computer, controlled. Based on inputs from sensors, the computer controls the amount of resistance provided by the actuator in order to adapt to changes in terrain and gait speed and decide when the transition from stiff to loose, or vice versa, should occur, thereby increasing safety, improving gait symmetry, and increasing energy efficiency. Current prosthetic knees that incorporate computer controlled actuators are relatively complex and heavy, which both increases cost and is burdensome to the user. Among the attempts to address the instant problems are found the following U.S. Pat. Nos. 6,764,520 B2, 6,755,870 B1; 6,740,125 B2; 6,719,806 B1; 6,673,117 B1; 6,610,101 B2, 6,517,585 B1; 6,423,098 B1; 6,113,642; 5,888,212; 5,571,205; and 5,383,939, each of which differs from the instant teachings.

It should, therefore, be appreciated that there exists a continuing need for a prosthetic knee that provides the gait speed adaptability and safety of a computer controlled knee but is relatively lightweight and simple in design. The present disclosure fulfills this need and others.

SUMMARY OF THE DISCLOSURE

A prosthetic knee provides a single axis of rotation and includes a hydraulic damping cylinder, a microprocessor, and sensors. Based on input from the sensors, the microprocessor selects a flow path within the hydraulic cylinder in order to provide the proper amount of knee resistance to bending for a given situation. The resistance of each flow path within the hydraulic cylinder is manually preset. Changes in gait speed are accommodated by employing a hydraulic damper with intelligently designed position sensitive damping. Moreover, the knee need not be un-weighted to transition from the stance phase to the swing phase of gait. As a result, the knee safely provides a natural, energy efficient gait over a range of terrains and gait speeds and is simpler, less costly, and lighter weight than the prior art.

Disclosed is a prosthetic knee system comprising, in combination, a frame, a computer, a rotor connected to the frame providing at least one axis of rotation about the prosthetic knee and using a hydraulic damping cylinder that compresses or extends to facilitate resistance to rotation, the hydraulic damping cylinder further comprising: a prosthetic knee flexion resistance path and a prosthetic knee extension resistance path; wherein at least one of the flexion resistance path and the extension resistance path further comprises a plurality of flow resistance paths; and wherein the computer determines the resistance of the flow resistance path.

Similarly disclosed is a prosthetic knee system, comprising, in combination a frame, a computer, a rotor connected to the frame providing at least one axis of rotation about the prosthetic knee and using a hydraulic damping cylinder to facilitate resistance to rotation, the hydraulic damping cylinder further comprising: a low force flexion resistance flow path; a high force flexion resistance flow path; and an extension resistance flow path, wherein the high force flexion resistance flow path is the knee's default and the computer determines when to use the low force flexion resistance flow path.

Still further disclosed is a improved prosthetic knee device comprising a computer and a plurality of parallel flow paths of varying flow resistance.

In yet another aspect of the present disclosure, a method of mimicking a human gait with a computer and sensor disposed in a prosthetic knee is disclosed comprising, in combination, providing a prosthetic knee with variable damping, wherein the variable damping comprising at least: waiting for a maximum force to be registered in a heel sensor; waiting for a maximum force to be registered in a toe sensor; and initiating a second trigger.

Finally disclosed is a prosthetic knee comprising a frame and a rotor connected to the frame providing at least one axis of rotation about the prosthetic knee and using a hydraulic damping cylinder with position sensitive damping to facilitate resistance.

DRAWINGS

Embodiments of the present disclosure will now be described, by way of example only, with reference to the following drawings in which.

DETAILED DESCRIPTION

Figure 1:
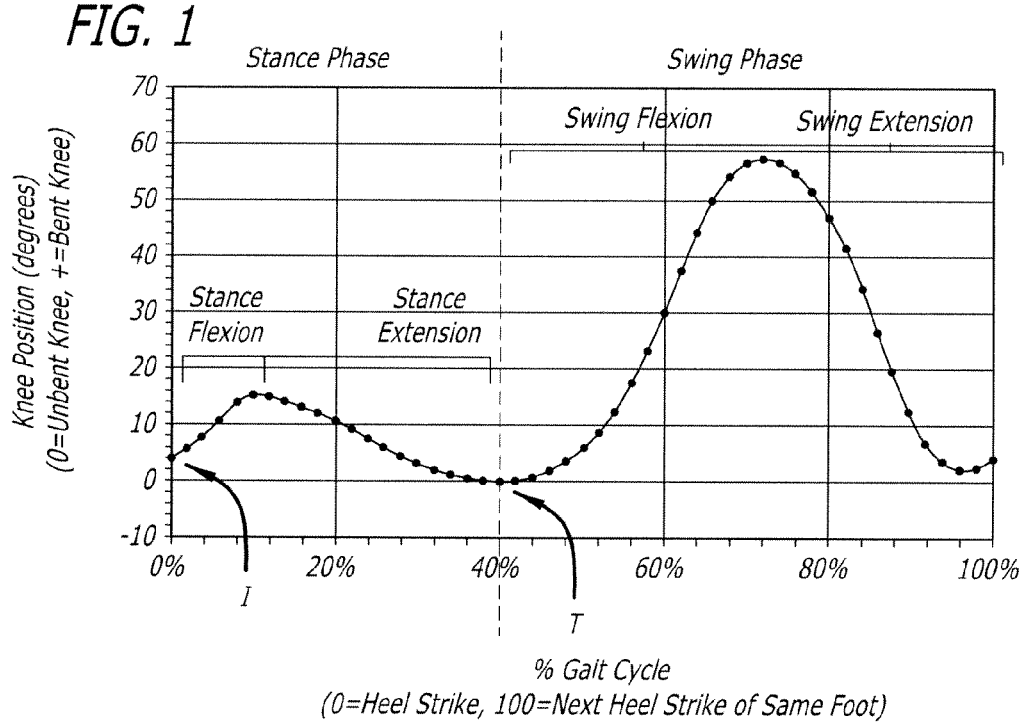
FIG. 1 is a graph of an exemplary walking gait cycle on level ground for an observed leg, in which knee position is provided along the y-axis and percentage of gait cycle is provided along the x-axis.

Makers of prosthetic knees have long attempted to mimic a natural walking gait. For purpose of illustration, this may be understood to be a reference to an exemplary walking gait cycle (level ground) as is graphically presented in FIG. 1. The chart depicts the knee position, along the y-axis, for an observed leg with respect to a percentage of gait cycle, along the x-axis. In the graph, the gait cycle initiates as the heel of the observed leg strikes the ground.

For each leg, a walking gait can be divided into two phases, a stance phase and a swing phase. The stance phase is defined as the period of time during which the foot of the observed leg is weighted. The swing phase is defined as the period of time when the foot of the observed leg is un-weighted. As a point of reference, the transition (T) from the stance phase to swing phase occurs at about 40 percent of the gait cycle.

The stance phase of a walking gait begins as the heel strikes the ground, indicated by point (I) on the graph. Upon heel strike, the knee flexes slightly to absorb some of the impact forces acting on the limb due to weight acceptance—referred to as "stance flexion" of the knee.

After the foot is flat on the ground, the shin begins to rotate forward about the ankle. As the shin rotates, the knee remains flexed in order to minimize the rise of the person's center of mass as it passes over the ankle joint center. As the shin continues to rotate forward and the center of mass progresses forward, the weight acting on the limb moves towards the toe of the foot. The force of the weight acting on the toe generates a torque about the knee joint that tends to straighten, or extend, the knee—referred to as "stance extension" of the knee. Stance extension continues until the transition point to the swing phase.

Soon after the knee is completely extended, the toe pushes off the ground, stance ends, and swing begins. As the toe pushes off the ground, the knee rapidly flexes to about 60 degrees—referred to as "swing flexion" of the knee. In order to keep the toe from stubbing on the ground, the knee will remain flexed as the leg rotates, or swings, forward about the hip joint. As the leg continues to swing forward the knee will extend until it is nearly straight—referred to as "swing extension" of the knee. Soon after the knee is fully extended, the heel of the foot will strike the ground again, and the gait cycle begins all over.

During the level-ground walking gait cycle described above, the knee, together with the muscles acting on it, functions primarily as an absorber of energy. In attempts of achieving a natural walking gait, it has been known to incorporate hydraulic dampers in prosthetic knees to control the motion of the knee joint during both the stance and swing phases of the gait cycle. In such prosthetic knees, during the stance phase, the hydraulic damper provides a relatively high amount of resistance to motion, or damping, making the knee joint comparatively stiff and able to support high forces. During the swing phase, the hydraulic damper provides a relatively low amount of resistance making the knee joint comparatively loose and able to swing freely. Thus, generally speaking, such prosthetic knees have both a stiff configuration and a loose configuration. To achieve a natural, energy efficient gait the hydraulic damper must provide the proper amount of resistance in each of these configurations, and the transition between these configurations must occur quickly and at the proper time in the gait cycle. In addition, to insure safety the transition should never occur when the user is not walking and the prosthetic limb is weighted.

In current prosthetic knees that use passive mechanical hydraulic dampers, the amount of resistance provided by the damper is controlled in both the stiff and the loose configurations by metering the flow of hydraulic fluid through valves that are manually set. The transition between the stiff and loose configurations is triggered by the occurrence of mechanical events (e.g., full extension of the hydraulic cylinder and reversal of hydraulic flow). There are two major drawbacks of knees designed this way: (1) the amount of resistance provided by the hydraulic damper is optimal for only a single gait speed and; (2) the mechanical events that trigger the transition from stiff to loose, or vice versa, can occur at the wrong time and thereby introduce a safety hazard.

The present disclosure presents a novel way to actively and dynamically control hydraulic dampers in prosthetic knees. According to embodiments of the present disclosure, a computer selects various flow paths. The various flow paths provide varying degrees of resistance to a flow fluid. Controlling the flow path allows the computer to selectively dampen a hydraulic damping cylinder and consequently vary the resistance of the prosthetic knee depending on the phase of the gait cycle.

Figure 2:
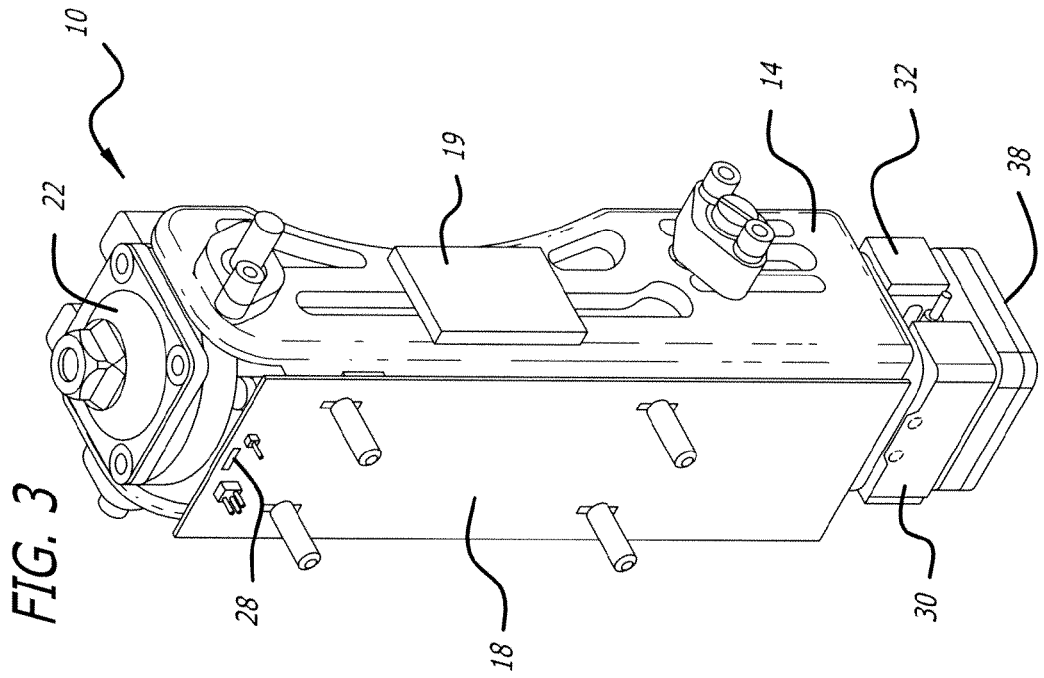
FIG. 2 is a back perspective view of a prosthetic knee in accordance with the disclosure.
Figure 3:
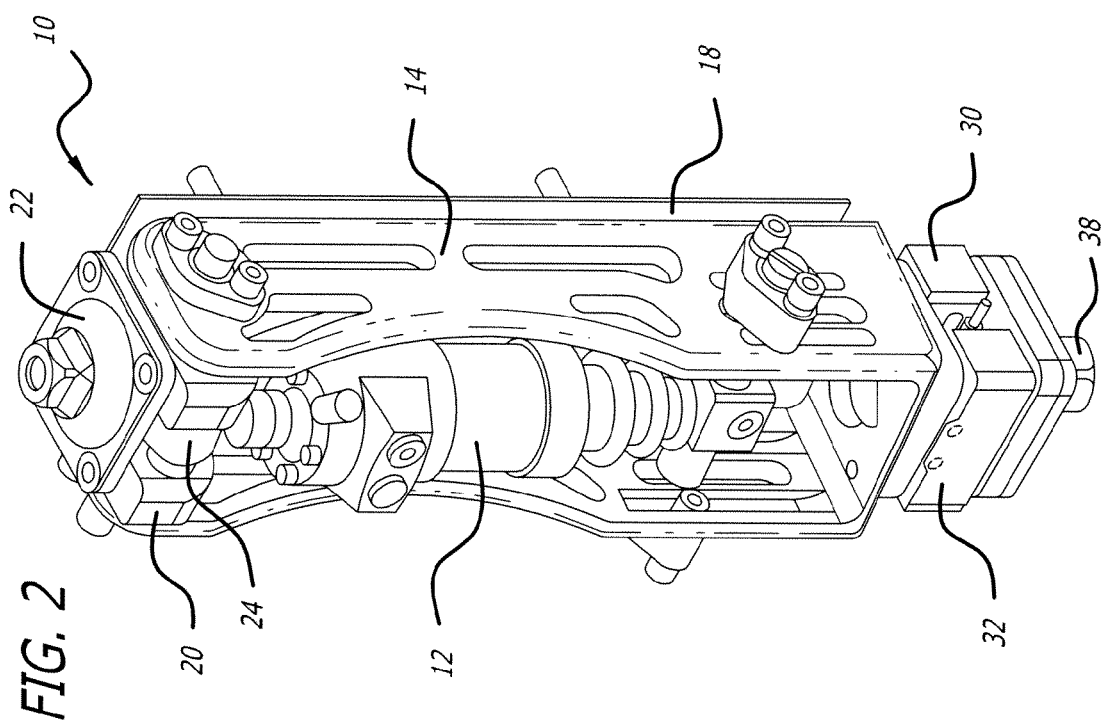
FIG. 3 is a front perspective view of the prosthetic knee of FIG. 2.
Figure 6:
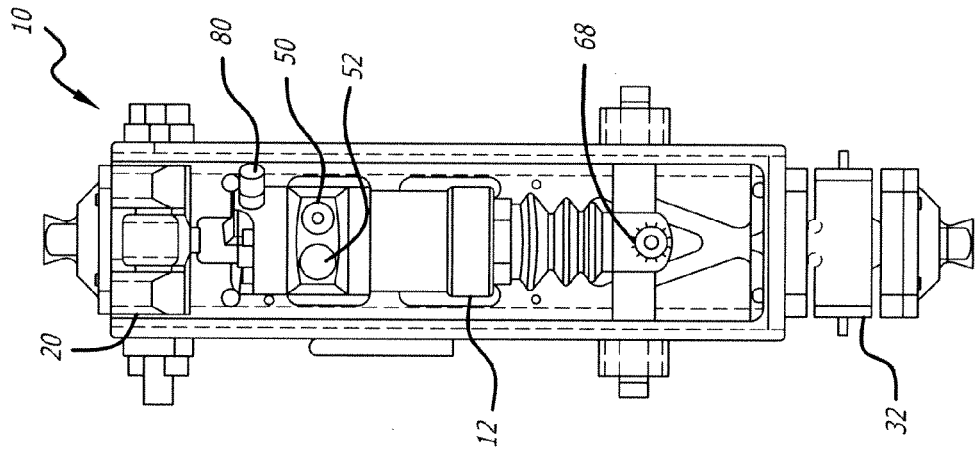
FIG. 6 is a back elevational view of the prosthetic knee of FIG. 2.
Figure 5:
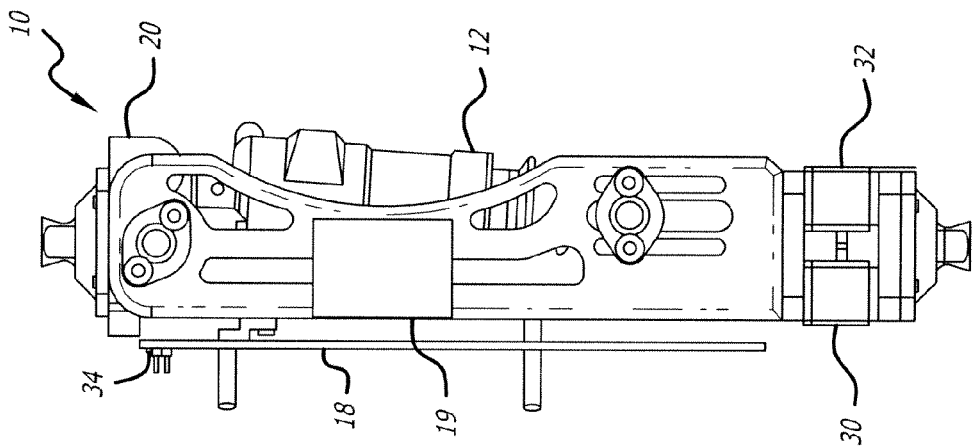
FIG. 5 is a right-side elevational view of the prosthetic knee of FIG. 2.
Figure 4:
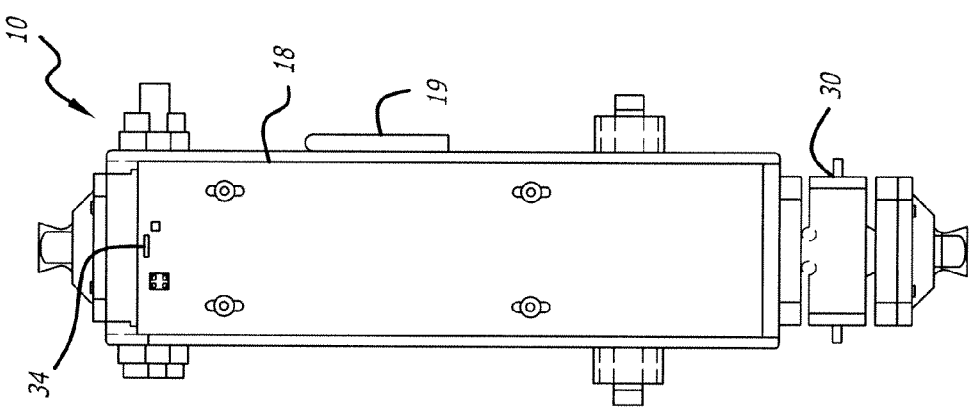
FIG. 4 is a front elevational view of the prosthetic knee of FIG. 2.
Figure 11:
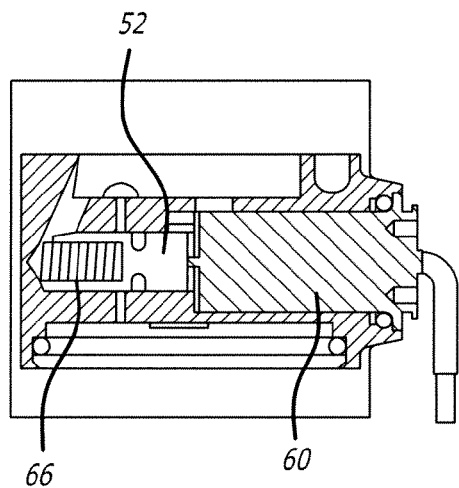
FIG. 11 is a cross-sectional view of the spool valve and solenoid of the hydraulic cylinder of FIG. 9A.
Figure 12:
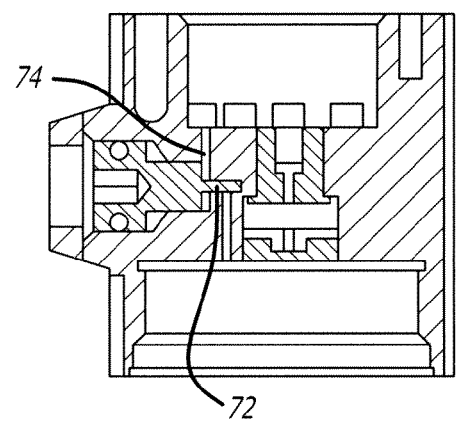
FIG. 12 is a cross-sectional view of the high force compression, or stance flexion, resistance adjustor of the hydraulic cylinder of FIG. 9A.

Referring now to an embodiment shown in FIG. 2, there is shown prosthetic knee 10 having hydraulic damping cylinder 12 disposed in frame 14. In the exemplary embodiment, hydraulic damping cylinder 12 may be any damping cylinder that would be well known to a person of ordinary skill in the art. As depicted in FIG. 11, the hydraulic damping cylinder contains normally-closed, solenoid-actuated spool valve 52. The state of spool valve 52 is controlled via a processing system having a digital processor, or computer (not shown), mounted on a printed circuit board (PCB) 18, which communicates with sensors disposed about the knee. Power is provided by battery pack 19 mounted on frame 14 or in another suitable location. As discussed below, using input from the sensors the processing system controls via spool valve 52, the transition from when the knee joint is stiff to when it is loose ensuring safe operation of the knee.

Referring again to FIG. 2, prosthetic knee 10 includes rotor 20 mounted to frame 14, defining a knee joint center about which the knee bends. Rotor 20 is attached to a proximal end of frame 14 such that proximal mount 22 can be attached to rotor 20. Proximal mount 22 is configured to mate with a limb socket (not shown) that is conformed to the user's remnant limb.

Hydraulic damping cylinder 12 is attached at its proximal end to rotor 20 and at its distal end to frame 14, allowing hydraulic damping cylinder 12 to regulate knee movement. Thus, according to an embodiment of the instant teachings, when the knee angle is increasing, hydraulic damping cylinder 12 is being compressed, and when the knee angle is decreasing, hydraulic damping cylinder 12 is being extended.

Sensors located throughout frame 14 detect and convey data to the computer. Extension sensor 28 is spaced about the knee to sense the relative position of the knee joint. In the exemplary embodiment, extension sensor 28 is disposed about the proximal end of the knee and includes a magnetic reed switch attached to the PCB 18 and a magnet attached to rotor 20 in spaced relationship to the magnetic reed switch. When the knee is fully extended, i.e., knee angle of about zero degrees, the magnetic reed switch is disposed near the magnet. As the knee is bent, the reed switch and the magnet rotate away from each other. Input from the magnetic reed switch is provided to the computer system. As a result, the computer can determine when the knee is fully extended.

Likewise, front load sensor 30 and rear load sensor 32, are disposed in a distal end of prosthetic knee 10 between frame 14 and distal mount 38, to which attaches a lower leg prosthesis (not shown). These load sensors determine how much load is being applied and the distribution of the load on the foot throughout the gait cycle. For example, as the heel strikes the ground at the beginning of the gait cycle, rear load sensor 32 will detect a compressive load and front load sensor 30 will detect a tensile load. Then, as the weight shifts from heel to toe during the stance phase of the gait cycle, the load detected by rear load sensor 32 will become a tensile load while the load detected by front load sensor 30 will become a compressive load. As a result, the computer can determine when the transition from the stance phase to the swing phase of the gait cycle should occur and actuate spool valve 52 of the hydraulic damping cylinder 12 at the proper time, as described below.

Figure 7:
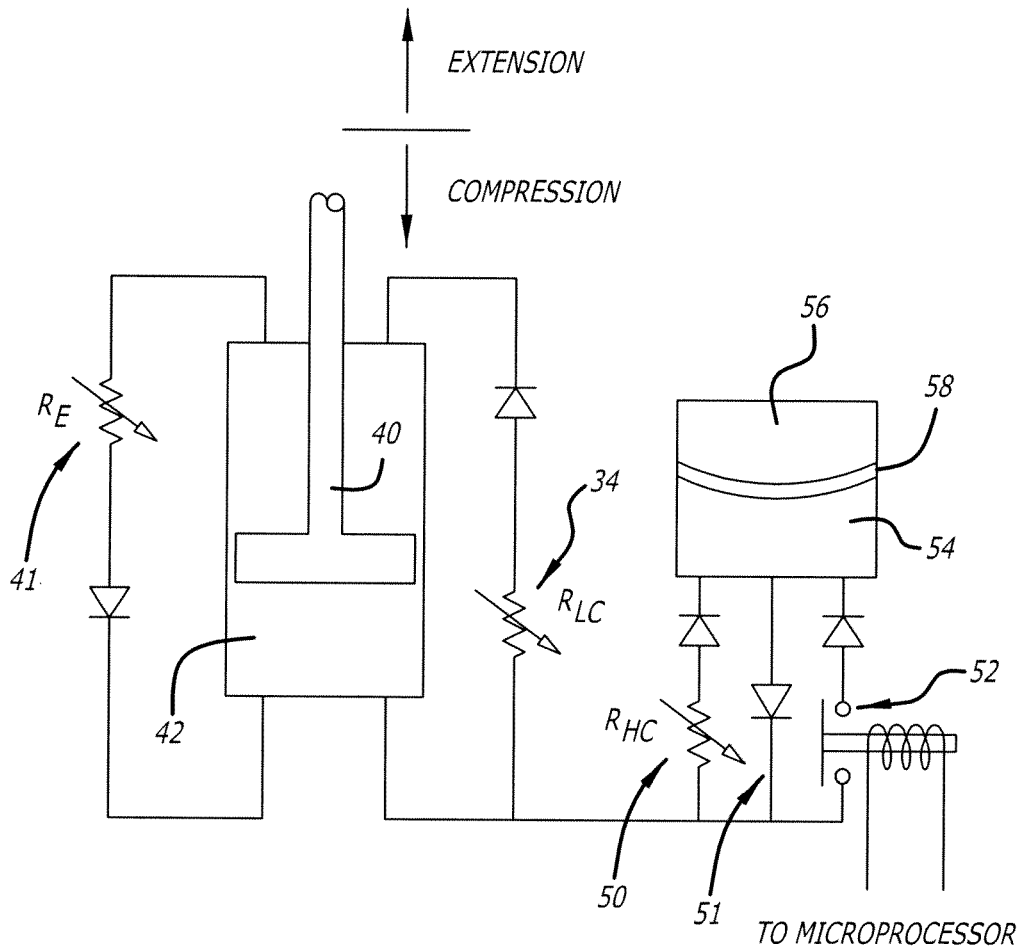
FIG. 7 is a simplified schematic describing an exemplary operation of the hydraulic cylinder of FIG. 9A.
Figure 9B:
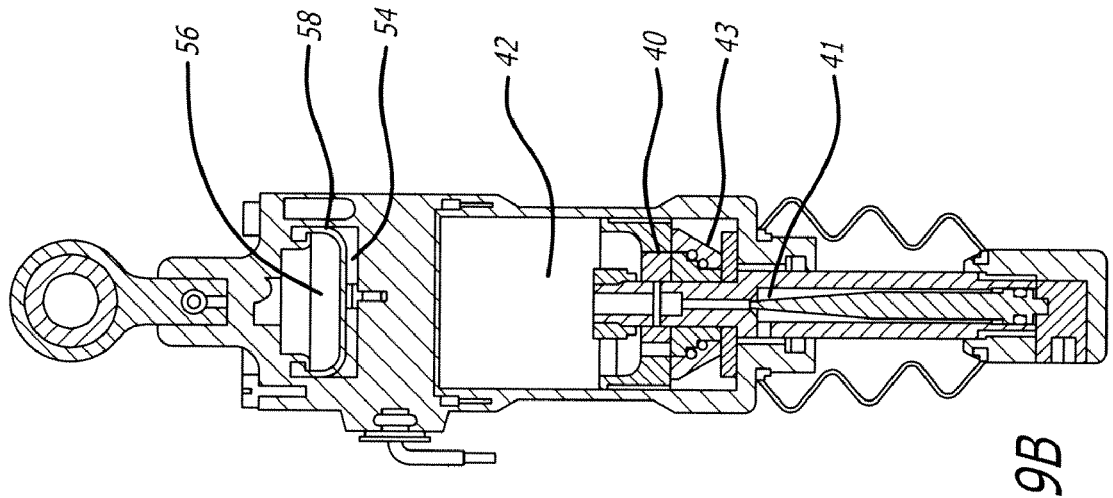
FIG. 9B is a cross-sectional view of the hydraulic cylinder of FIG. 9A.
Figure 9A:
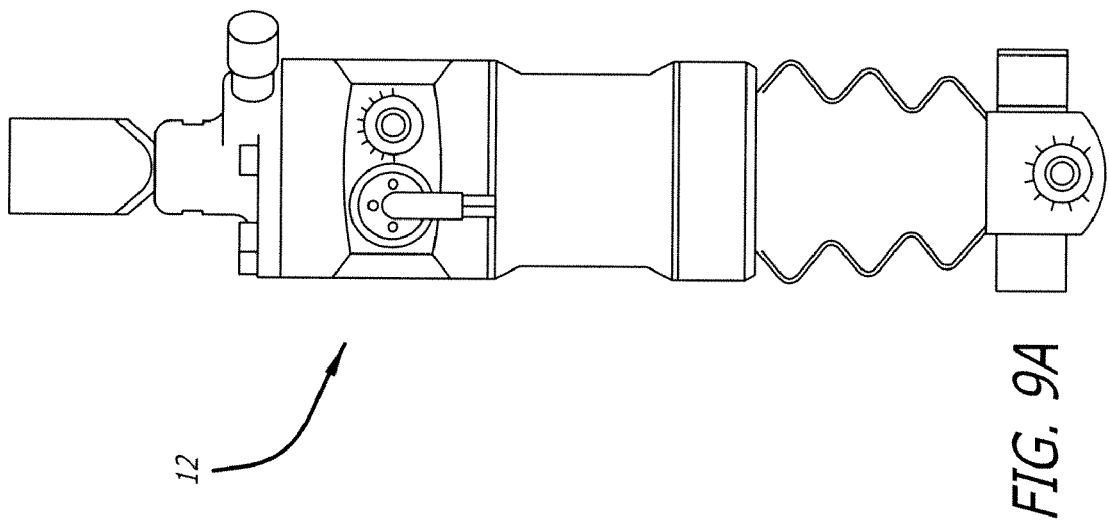
FIG. 9A is a back elevational view of the hydraulic cylinder of the prosthetic knee of FIG. 2.
Figure 10:
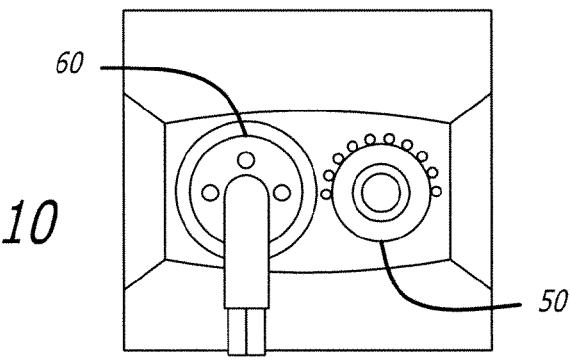
FIG. 10 is a close-up, back elevational view of the hydraulic cylinder of FIG. 9A, depicting the solenoid and high force compression, or stance flexion, resistance adjustor (needle valve).

FIG. 7 depicts a simplified schematic of the hydraulic circuit within hydraulic damping cylinder 12. Hydraulic damping cylinder 12 includes piston 40 mounted for axial movement within main fluid chamber 42 and a fluid, which may be any hydraulic fluid, such as bicycle or motorcycle shock fluid, known to a person of ordinary skill of the art. Progressive-type hydraulic cylinders, including Mauch-type cylinders, may be used in which the cylinder damping changes as the angle of the knee joint changes. The choice of cylinder will be readily apparent to a person of ordinary skill in the art depending on the desired characteristics of the hydraulic cylinder.

As the piston moves in the direction of compression, fluid flows through two paths. Some fluid flows out of main chamber 42 into fluid reservoir 54 through first needle valve 50, which provides high force compression, or stance flexion, resistance ($R_{HC}$). The rest of the fluid flows across the piston through a pressure sensitive control valve 34 that provides the low force compression, or swing flexion, resistance $R_{LC}$. In embodiment, pressure sensitive valve 34 is a progressive damping valve as disclosed in U.S. Pat. Nos. 5,190,126 and 6,978,872, both of which are incorporated by reference as if fully disclosed herein. Progressive damping allows prosthetic knee 10 to mimic a more natural swing during swing flexion.

In a normal human gait, swing flexion is arrested at approximately 60 degrees from a straight leg. During the initial swing flexion phase through about 30 degrees, the leg swings freely. However, from about 30 degrees to about 60 degrees the brain decelerates the swing until it is arrested at about 60 degree. According to an embodiment of the present disclosure, there is utilized a progressive damping system to mimic the natural effect in prosthetic knees. The progressive damping system comprises specialized pressure sensitive control valve 34 ($R_{LC}$) disclosed in the above referenced patents. Pressure sensitive control valve 34 allows mostly free swing between about 0 degrees and about 30 degrees and thereafter progressively dampens movement by increasing resistance until arrest of swing flexion at about 60 degrees.

Normally-closed, solenoid-actuated spool valve 52 is parallel to first needle valve 50. Therefore, when spool valve 52 is opened, flow bypasses first needle valve 50, essentially eliminating the high force compression resistance. As piston 40 moves in the direction of extension, fluid again flows through two paths. Some fluid flows from fluid reservoir 54 back into main fluid chamber 42 via check valve 51 with very little resistance. The rest of the fluid flows across piston 40 through second needle valve with shim stack 41, which provides extension, or swing extension, resistance ($R_E$).

Both the high force compression resistance ($R_{HC}$) and the extension resistance ($R_E$) may be adjusted by the user by manually changing the position of first needle valve 50 and second needle valve with shim stack 41, respectively. Gas chamber 56 is filled with a gas, typically air, and disposed adjacent to fluid reservoir 54, separated by flexible bladder 58. The low force compression resistance ($R_{LC}$) is regulated by the user by changing the pressure in the gas chamber, in embodiments. In other embodiments, an independent floating piston may replace gas chamber 56 and bladder 58 to accomplish the same purpose and would be understood by a person of ordinary skill in the art.

Figure 13:
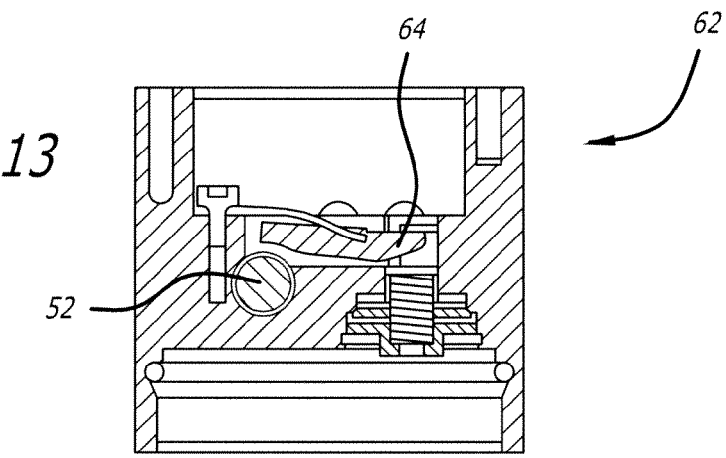
FIG. 13 is a cross-sectional view of the latching mechanism of the hydraulic cylinder of FIG. 9A.

Spool valve 52 is actuated by solenoid 60. When solenoid 60 is de-energized, return spring 66 holds spool valve 52 in a closed position. Energizing solenoid 60 causes the spool to move in the direction opposite to the force of return spring 66, thereby opening spool valve 52. When spool valve 52 achieves an open position, latching mechanism 62, shown in FIG. 13, prevents return spring 66 from closing spool valve 52. In an embodiment, latching mechanism 62 includes cantilever beam 64. However, other approaches may be used, as would be known to a person of ordinary skill in the art. When hydraulic flow reverses, latching mechanism 62 releases spool valve 52 and return spring 66 moves the spool to the closed position, thereby closing spool valve 52.

Operation of hydraulic damping cylinder 12 during a normal walking gait cycle works in conjunction with the operation of the valves. As heel strike occurs, the ground reaction forces may tend to bend prosthetic knee 10 and compress hydraulic damping cylinder 12. At this moment, solenoid 60 is de-energized thus spool valve 52 is closed and the fluid flows through both the first needle valve 50 and the low force resistance channel ($R_{HC}$ and $R_{LC}$). Therefore, hydraulic damping cylinder 12 provides a high amount of damping causing the knee joint to be relatively stiff and able to support the user's weight. As the user's weight begins to come off the foot at the end of the stance phase the computer energizes solenoid 60 to open spool valve 52, which bypasses the high force resistance of first needle valve 50. Once latching mechanism 62 engages and is holding spool valve 52 open, solenoid 60 is de-energized to conserve energy. According to embodiments, the transition between high resistance compression and low resistance compression occurs in 10 ms or less. With spool valve 52 open, the damping decreases allowing prosthetic knee 10 to bend rapidly during swing flexion. As the lower leg swings forward and swing extension begins, the direction of hydraulic flow within the cylinder is reversed, and latching mechanism 62 releases the spool. Return spring 66 then closes spool valve 52, which causes hydraulic damping cylinder 12 to once again be able to provide a high amount of damping when the heel strikes the ground at the start of the next gait cycle.

Figure 8:
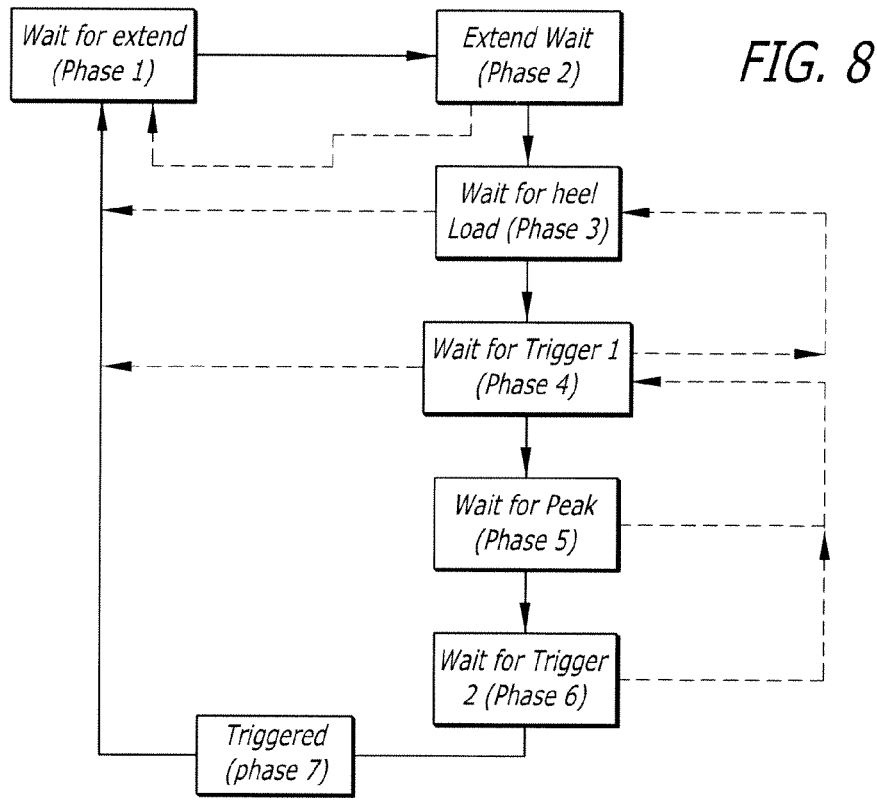
FIG. 8 is a simplified block diagram describing an exemplary operation of the software to control the solenoid-actuated spool valve of the hydraulic cylinder of FIG. 9A.

With reference now to FIG. 8, a computer system controls the damping of prosthetic knee 10. According to an embodiment, the computer is an interrupt driven state machine that runs a control algorithm. The interrupt cycle time is 1 ms, or 1000 Hz. The computer allows only a single state change per cycle. Generally, the main function and output of the computer is to switch the knee between a stiff configuration and a freely swinging configuration, which is accomplished by the computer control of solenoid 60. Sensors disposed in frame 14 of prosthetic knee 10 provide the computer with the input required to energize solenoid 60 at the proper time during the gait cycle.

According to an embodiment, extension sensor 28 is digital. Thus, at each interrupt, the computer reads the state of extension sensor 28. Conversely, both front load sensor 30 and rear load sensor 32 are analog sensors. Consequently, the computer uses a two interrupt sequence to obtain a digital signal from the analog load sensors. At the first interrupt, an analog to digital conversion algorithm is initiated using data from each load sensor. At the second interrupt, the computer retrieves the digital data output from the analog to digital conversion algorithm. Once the computer has digital readings from the load sensors, the computer calculates a load calculation and difference of a moment calculation.

The load calculation tells the computer whether the foot, shin, and knee are loaded. In an embodiment, the load is calculated by adding the output of front load sensor 30 and rear load sensor 32. The moment calculation takes the difference between front load sensor 30 and rear load sensor 32. When the heel is predominantly weighted, the moment calculation is negative. However, when the toe is predominantly weighted, the moment calculation is positive. The computer uses the load calculation and the moment calculation to determine the amount of damping to apply to the knee. Specifically, the state machine uses data from the sensors in conjunction with a timer algorithm to advance through progressive phases of a control algorithm.

The control algorithm controls solenoid 60, which actuates spool valve 52. Each cycle begins just before heel strike at phase 1 of FIG. 8 and ends at phase 7 when the computer causes solenoid 60 to be energized. A short time before the heel of the foot strikes the ground, the knee becomes fully extended. Extension sensor 28 detects the straightened leg and communicates a signal to the computer. According to an embodiment, the sensor detects a straightened leg when the knee is within 5 degrees of full extension. Phase 1 is the default start state in the exemplary embodiment.

Once an extend signal is detected from extension sensor 28, the algorithm advances to phase 2. During phase 2, the computer allows a set period of time to elapse. The period of time is customizable by individual users, although the default timing will be appropriate for most users. The processing system will not proceed to phase 3 until the set time period elapses, after which the algorithm will automatically advance to phase 3.

Certain conditions, however, will cause phase 2 to either reset the period of time that must elapse before phase 3 or return the algorithm to phase 1. According to embodiments, the algorithm will return to phase 1 or 2 if the load drops below a set minimum value or the extension sensor 28 is sensed in an open position. Whether the algorithm returns to phase 1 or phase 2 is inconsequential and is a matter of preference for the implementer of the algorithm because extension sensor 28 is closed, which will, upon returning to phase 1, trigger the algorithm to automatically advance to phase 2. Thus, the only difference between whether the algorithm returns to phase 1 or resets phase 2 is that returning the algorithm to phase 1 will cause a delay of one cycle, or 1 ms, before phase 1 advances to phase 2.

During phase 3 the computer monitors the load reading from front load sensor 30 and rear load sensor 32 and waits for a "heel moment." During phase 3 the algorithm waits until the load is predominantly on the heel. According to an embodiment, a "heel moment" occurs when the moment calculation is at a minimum. Once a "heel moment" event occurs, the algorithm then advances to phase 4. If, during phase 3, the load drops below a set minimum value or the extension sensor 28 is sensed in an open position, then the algorithm will return to either phase 1 or phase 2, as previously described.

During phase 4 the load is in the process of transferring from the heel to the toe. The computer monitors the moment calculation. Once it exceeds a set value, for example ⅔ of the max moment calculation (i.e., a given load is shifted from heel to toe), the algorithm advances to phase 5. The computer times phase 4. If the moment calculation fails to exceed the set value before a set time elapses, then the algorithm returns to phase 3. If, during phase 4, the load drops below a set minimum value or the extension sensor 28 is sensed in an open position at the start of phase 4, the algorithm returns to phase 1 or phase 2, as previously described. In embodiments, the moment calculation value that must be exceeded to advance to phase 5 is adjustable on a per user basis.

If, during phase 4, the extension sensor 28 opens before the value of the moment calculation exceeds the set value, then phase 4 proceeds with a modified set of values for the remainder of the cycle optimized for descending type movement, such as moving down inclined surfaces. According to embodiments, these values may be adjusted on a per user basis. By adjusting the values for descending type movement, the knee will be able to swing to prevent toe stubbing, improving safety. Generally, the value of the moment calculation that must be exceeded to proceed to phase 5 for descending type movement will be set lower than the normal, level ground value because the load will be more focused on the heel than the toe in these types of situations.

During phase 5 the algorithm waits until the moment calculation reaches a maximum. The algorithm then proceeds to phase 6 once it detects that the moment calculation drops below the measured maximum. Various criteria may be used, according to embodiments, to determine when to advance to phase 6, for example, including when the moment calculation drops below a preset percentage of the maximum, when the moment calculation minus a preset value is lower than the maximum, or when the moment calculation is less than a preset trigger point. In the latter case, the algorithm may advance directly to phase 7, in embodiments.

During phase 6, the algorithm monitors the moment calculation. Once it drops below a preset trigger point, the algorithm advances to phase 7 and energizes solenoid 60 for swing flexion and extension. After triggering solenoid 60, the algorithm advances to phase 1 and awaits the closing of extension sensor 28, which starts the control cycle over. The preset trigger point is adjustable on a per user basis and may have variable values for normal movement and descending type movements.

According to embodiments, users may personalize the timing settings of the timed phases. Control of the computer settings may be accomplished by use of a Bluetooth signaling mechanism, for example. According to exemplary embodiments, the computer on the knee integrates a Bluetooth receiver that receives signals from a computer device containing a Bluetooth transceiver. Examples of suitable computer may be a home PC or a PDA. Software compiled specifically for the computer platform, for example a PDA, allows a user to monitor and adjust settings for the timings of the applicable phases. Setting data may be stored in flash memory or an equivalent electronic storage media within prosthetic knee 10. Adjustment of the trigger points and other user configurable variables may be similarly accomplished.

The present disclosure has been described above in terms of presently preferred embodiments so that an understanding of the present disclosure can be conveyed. However, there are other embodiments not specifically described herein for which the present disclosure is applicable. Therefore, the present disclosure should not to be seen as limited to the forms shown, which is to be considered illustrative rather than restrictive.

The invention claimed is:

1. A device, comprising, in combination:
   a prosthetic knee comprising:
      a frame;
      a computer;
      a hydraulic damping cylinder; and
      a rotor connected to the frame;
   wherein the rotor provides at least one axis of rotation about the prosthetic knee and wherein the hydraulic damping cylinder facilitates resistance to rotation, the hydraulic damping cylinder further comprising:
a low force flexion resistance flow path;
a high force flexion resistance flow path; and
an extension resistance flow path,
wherein the high force flexion resistance flow path is the knee's default flow path and the computer determines when to use the low force flexion resistance flow path.

2. The device of claim 1, wherein in the low force flexion resistance flow path a hydraulic fluid exits a main cylinder chamber and passes through a spool valve into a reservoir having a compressible gas chamber disposed adjacent thereto.

3. The device of claim 2, wherein activating a solenoid allows hydraulic fluid to bypass the high force flexion resistance flow path by effecting the opening of the spool valve for the duration of the low force cycle.

4. The device of claim 3, wherein once the spool valve opens, a latching mechanism is triggered, the latching mechanism holding the spool valve opened after the solenoid is deactivated.

5. The device of claim 4, wherein upon a reversal of the hydraulic fluid flow, the latching mechanism releases the spool valve causing the spool valve to close, and a needle valve allows hydraulic fluid to flow through an extension piston bypass resistance flow path into the main fluid chamber, whereby resistance in the extension resistance flow path can be manually adjusted with the needle valve.

6. The device of claim 5, wherein once the spool valve is released, a return spring causes the spool valve to close.

7. The device of claim 5, further comprising one or more check valves that inhibit back flow through the hydraulic fluid flow paths.

8. The device of claim 1, further comprising at least one sensor, wherein the at least one sensor provides useful data to the computer.

9. The device of claim 8, wherein the sensors comprise at least:
an extension sensor, the extension sensor providing useful data to the computer regarding the relative position of the prosthetic knee joint;
a front load sensor, the front load sensor providing useful data to the computer regarding load on a foot; and
a rear load sensor, the rear load sensor providing useful data to the computer regarding load on the foot.

10. The device of claim 8, wherein the computer regulates damping within the hydraulic damping cylinder, the computer receiving data from the sensors and in response causing triggering the high force flexion resistance flow path or the low force flexion resistance flow path during flexion of the prosthetic knee.

11. The device of claim 2, wherein a reservoir is separated by a physical bladder forming an adjustable fluid chamber and an adjustable compressible gas chamber, and wherein resistance of the low force flexion resistance flow path is regulated influenced by a gas pressure of a gas in the adjustable compressible gas chamber.

12. The device of claim 2, wherein resistance of the low force flexion resistance flow path is regulated in part by manual adjustment of an adjustable needle valve in a low force compression piston bypass resistance flow path.

13. The device of claim 1, wherein the hydraulic damping cylinder is a hydraulic damping cylinder with position sensitive damping.

14. The device of claim 13, wherein the hydraulic damping cylinder minimizes damping during a swing flexion phase of knee movement from about 0 to about 30 degrees and progressively increases damping from about 30 degrees to about 60 degrees,
wherein resistance stops flexion of the prosthetic knee at about 60 degrees.

* * * * *